United States Patent
Hamada et al.

(10) Patent No.: US 7,427,688 B2
(45) Date of Patent: Sep. 23, 2008

(54) PRODUCTION METHOD OF OPTICALLY ACTIVE DIPHENYLALANINE COMPOUNDS

(75) Inventors: Takayuki Hamada, Kawasaki (JP); Masanobu Yatagai, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/430,909

(22) Filed: May 10, 2006

(65) Prior Publication Data

US 2006/0270869 A1    Nov. 30, 2006

(30) Foreign Application Priority Data

May 10, 2005  (JP) ............... 2005-137637
Jul. 20, 2005  (JP) ............... 2005-209795

(51) Int. Cl.
*C07C 51/16*    (2006.01)
(52) U.S. Cl. .............. 562/411; 562/450; 562/405; 560/37
(58) Field of Classification Search .......... 562/411, 562/450, 405; 560/37
See application file for complete search history.

(56) References Cited

U.S. PATENT DOCUMENTS

| | | | | |
|---|---|---|---|---|
| 4,665,187 A | * | 5/1987 | Bottcher et al. | 546/255 |
| 4,761,495 A | * | 8/1988 | Wirth et al. | 560/41 |
| 4,766,109 A | * | 8/1988 | Czarniecki et al. | 514/17 |
| 5,198,548 A | | 3/1993 | Beylin et al. | |
| 2006/0270869 A1 | | 11/2006 | Hamada et al. | |
| 2007/0032658 A1 | | 2/2007 | Hamada et al. | |

FOREIGN PATENT DOCUMENTS

WO  WO 03/002531 A2  1/2003
WO  WO 2004/056764 A1  7/2004

OTHER PUBLICATIONS

J.-W. Chang, et al., "An Efficient Synthesis of N-Boc-D-Diphenylalanine From a Chiral Azirdine-2-Carboxylate", Heterocylces, vol. 57, No. 6, 2002, pp. 1143-1148.
H.G. Chen, et al., "Chiral Synthesis of D- and L-3,3-Diphenylalanine (DIP), Unusual Alpha-Amino Acids for Peptides of Biological Interest", Tetrahedron Letters, vol. 33, No. 23, 1992, pp. 3293-3296.
U.S. Appl. No. 11/979,110, filed Oct. 31, 2007, Hamada et al.
U.S. Appl. No. 11/979,108, filed Oct. 31, 2007, Hamada et al.

* cited by examiner

*Primary Examiner*—Yvonne Eyler
*Assistant Examiner*—Sudhakar Katakam

(74) *Attorney, Agent, or Firm*—Oblon, Spivak, McClelland, Maier & Neustadt, P.C.

(57) ABSTRACT

The present invention provides a production method including reacting a diphenylmethylene halide compound represented by the following formula (1) with a malonic acid diester compound represented by the following formula (2) in an organic solvent selected from N-methyl-2-pyrrolidone, N-ethyl-2-pyrrolidone and N,N-dimethylformamide, in the presence of a base selected from an alkali metal hydride and an alkali metal t-butoxide to give a diester compound represented by the following formula (3), and then subjecting the diester compound to hydrolysis and decarboxylation to give a diphenylalanine compound represented by the following formula (4).

According to the present invention, diphenylalanine compound (4) can be obtained industrially advantageously in a high yield.

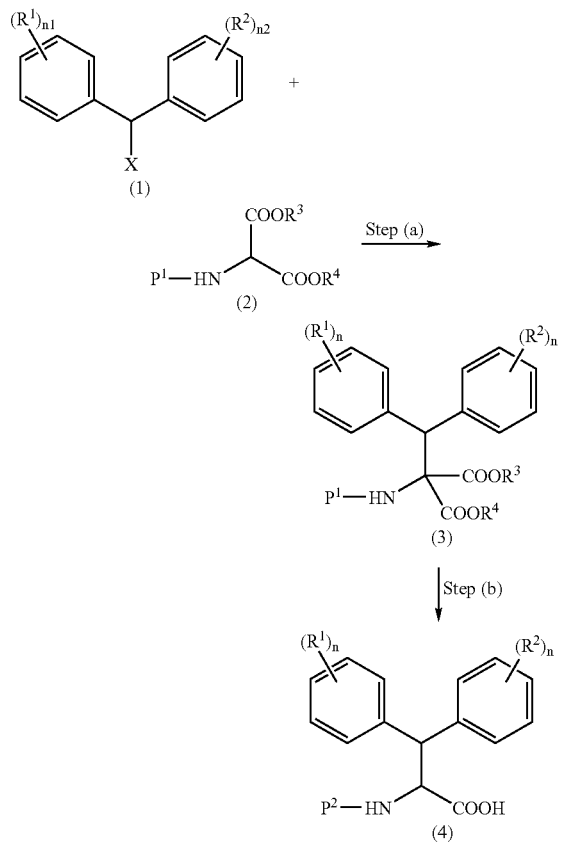

wherein each symbol is as defined in the specification.

10 Claims, 4 Drawing Sheets

US 7,427,688 B2

PRODUCTION METHOD OF OPTICALLY ACTIVE DIPHENYLALANINE COMPOUNDS

CROSS REFERENCES TO RELATED APPLICATIONS

This application claims priority to Japanese Patent Application No. 137637/2005, filed on May 10, 2005, and Japanese Patent Application No. 209795/2005, filed on Jul. 20, 2005.

TECHNICAL FIELD OF THE INVENTION

The present invention relates to diphenylalanine compounds and production methods thereof, and production methods of optically active diphenylalanine compounds useful as intermediates for anti-HIV drugs, dipeptidyl peptidase inhibitors and the like.

BACKGROUND OF THE INVENTION

A diphenylalanine compound, particularly an optically active diphenylalanine compound (including an amino group-protected compound thereof) is useful as an intermediate for pharmaceutical agents and has been used, for example, as an intermediate for anti-HIV drugs (WO04/056764) or dipeptidyl peptidase inhibitors (WO03/002531).

As a production method of 3,3-diphenylalanine, U.S. Pat. No. 4,766,109 describes, as shown in the following reaction scheme, a method comprising reacting diethyl acetamidomalonate with diphenylbromomethane in ethanol in the presence of sodium ethoxide to give diethyl 2-acetamido-2-(diphenylmethyl)malonate, subjecting the compound to hydrolysis in the presence of hydrogen bromide, neutralizing the reaction mixture with aqueous sodium hydroxide solution, and purifying the compound using a column to give 3,3-diphenylalanine, but the yield thereof is not concretely described.

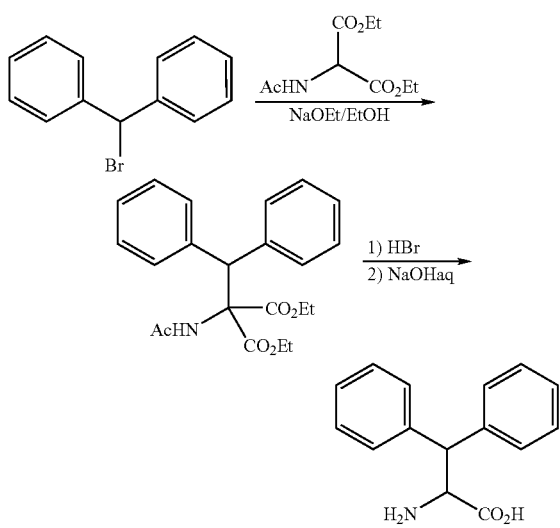

Thus, the present inventors tried production of 3,3-diphenylalanine by reacting diethyl acetamidomalonate with diphenylchloromethane or diphenylbromomethane according to the above-mentioned reaction scheme. However, diphenylmethyl ethyl ether was mainly obtained as a resultant product, and the objective compound, 3,3-diphenylalanine, could be obtained only in an extremely low yield.

As a different method, a method comprising reacting N-(diphenylmethylene)glycinate, which is synthesized from benzophenoneimine and glycinate, with diphenylbromomethane, as shown in the following reaction scheme, is known (U.S. Pat. No. 5,198,548).

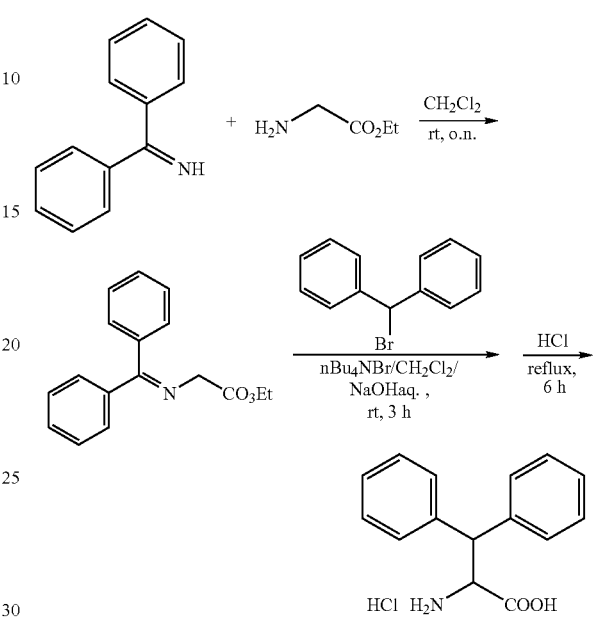

In the above-mentioned method, however, benzophenoneimine, which is a starting material compound, is difficult to obtain, and benzophenoneimine is used only as a leaving group. Therefore, this method is not necessarily considered to be an efficient production method effectively utilizing the starting material compound.

In the meantime, as a production method of optically active diphenylalanine, the aforementioned U.S. Pat. No. 5,198,548 describes a method of optical resolution of N-acetyldiphenylalanine with (−)-cinchonidine. However, this method achieves an inefficient yield of 25-30% in the optical resolution step. In addition, this patent describes a failure in the optical resolution of a 3,3-diphenylalanine compound by hog kidney acylase or carboxypeptidase.

As a still another method, *HETEROCYCLES*, vol. 57, No. 6, pp. 1143 (2002), and *Tetrahedron Letter*, vol. 33, No. 23, pp. 3293 (1992) describe asymmetric synthesis of N-Boc-diphenylmethylalanine. However, these methods require stoichiometric amounts of asymmetric sources, many steps, a low temperature reaction vessel to allow reaction at −78° C., and expensive reagents such as KHMDS, (potassium hexamethyldisilazane) and the like, which in turn increases the costs, and therefore, the methods are hardly industrially advantageous methods.

As mentioned above, a production method of an optically active diphenylalanine compound based on a biological technique has not been reported.

DISCLOSURE OF THE INVENTION

The present invention has been made in view of such factual situation and the problem to be solved is provision of a production method capable of industrially advantageously affording a diphenylalanine compound and an optically active diphenylalanine compound in a high yield. Moreover, the problem is provision of racemic N-acetyldiphenylalanine and racemic N-acetylbis(4-fluorophenyl)alanine as crystals.

The present inventors have conducted intensive studies in an attempt to solve the above-mentioned problems and found that a diphenylalanine compound can be conveniently obtained in a high yield by reacting a diphenylmethylene halide compound with a malonic acid diester compound in an organic solvent selected from N-methyl-2-pyrrolidone, N-ethyl-2-pyrrolidone and N,N-dimethylformamide, in the presence of a base selected from an alkali metal hydride and an alkali metal t-butoxide. In addition, they have also found that a penicillin amidase substrate-specifically reacts with a diphenylalanine compound having a particular structure, whereby an optically active diphenylalanine compound can be conveniently produced in a high yield. Furthermore, they have found that racemic N-acetyldiphenylalanine and racemic N-acetylbis(4-fluorophenyl)alanine can be crystallized by a particular method. Based on these findings, the present inventors have completed the present invention.

Accordingly, the present invention provides the following.

[1] A method of producing a diester compound represented by the following formula (3):

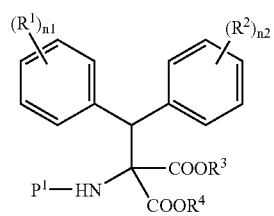

wherein $R^1$ and $R^2$ are each independently a halogen atom, an alkyl group, an alkoxy group, an amino group, a nitro group or a hydroxyl group, $n^1$ and $n^2$ are each independently an integer of 0-5, $R^3$ and $R^4$ are each independently an alkyl group or an aralkyl group, or $R^3$ and $R^4$ in combination form an alkylene group, and $P^1$ is an amino-protecting group, which comprises reacting a diphenylmethylene halide compound represented by the following formula (1):

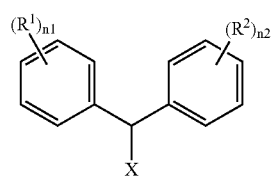

wherein $R^1$, $R^2$, $n^1$ and $n^2$ are as defined above, and

X is a chlorine atom, a bromine atom or an iodine atom, with a malonic acid diester compound represented by the following formula (2):

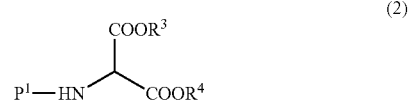

wherein each symbol is as defined above, in an organic solvent selected from N-methyl-2-pyrrolidone, N-ethyl-2-pyrrolidone and N,N-dimethylformamide, in the presence of a base selected from an alkali metal hydride and an alkali metal t-butoxide.

[2] The method of above-mentioned [1], wherein the base is selected from sodium hydride, sodium t-butoxide and potassium t-butoxide.

[3] The method of above-mentioned [1], wherein the organic solvent is selected from N-methyl-2-pyrrolidone and N-ethyl-2-pyrrolidone.

[4] The method of above-mentioned [1] to [3], wherein $R^1$ and $R^2$ are each a fluorine atom.

[5] The method of above-mentioned [1] to [4], wherein $R^3$ and $R^4$ are each an ethyl group.

[6] The method of above-mentioned [1] to [5], wherein $P^1$ is an acetyl group or a phenylacetyl group.

[7] The method of above-mentioned [1] to [6], wherein X is a chlorine atom or a bromine atom.

[8] The method of above-mentioned [1] to [7], which is carried out in the co-presence of an iodine compound or a bromine compound.

[9] The method of above-mentioned [1] to [7], which is carried out in the co-presence of a metal iodide or a quaternary ammonium iodide.

[10] A method of producing a diphenylalanine compound represented by the following formula (4) or a salt thereof, which comprises the following Steps (a) and (b);

Step (a): reacting a diphenylmethylene halide compound represented by the following formula (1):

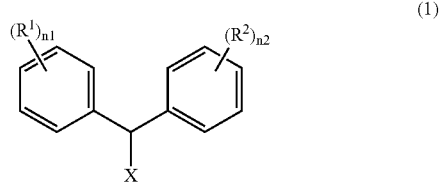

wherein $R^1$ and $R^2$ are each independently a halogen atom, an alkyl group, an alkoxy group, an amino group, a nitro group or a hydroxyl group, $n^1$ and $n^2$ are each independently an integer of 0-5, and X is a chlorine atom, a bromine atom or an iodine atom, with a malonic acid diester compound represented by the following formula (2):

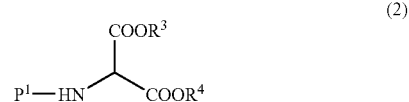

wherein
R³ and R⁴ are each independently an alkyl group or an aralkyl group, or R³ and R⁴ in combination form an alkylene group, and
P¹ is an amino-protecting group, in an organic solvent selected from N-methyl-2-pyrrolidone, N-ethyl-2-pyrrolidone and N,N-dimethylformamide, in the presence of a base selected from an alkali metal hydride and an alkali metal t-butoxide, to give a diester compound represented by the following formula (3):

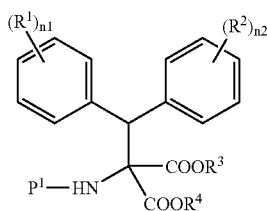

(3)

wherein each symbol is as defined above; and

Step (b): subjecting the diester compound to hydrolysis and decarboxylation, to give a diphenylalanine compound represented by the following formula (4):

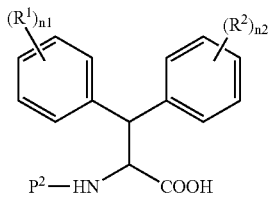

(4)

wherein
$R^1$, $R^2$, $n^1$ and $n^2$ are as defined above, and
$P^2$ is a hydrogen atom or an amino-protecting group, or a salt thereof.

[11] The method of above-mentioned [10], wherein P² is a hydrogen atom, an acetyl group or a phenylacetyl group.

[12] A method of producing an acyl-substituted diphenylalanine compound represented by the following formula (6):

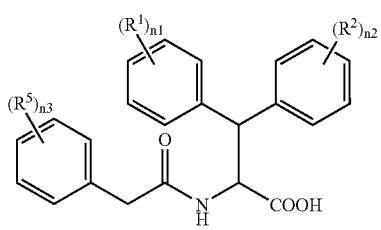

(6)

wherein
$R^1$, $R^2$ and $R^5$ are each independently a halogen atom, an alkyl group, an alkoxy group, an amino group, a nitro group or a hydroxyl group, and
$n^1$, $n^2$ and $n^3$ are each independently an integer of 0-5, or a salt thereof, which comprises converting P² of a diphenylalanine compound represented by the following formula (4):

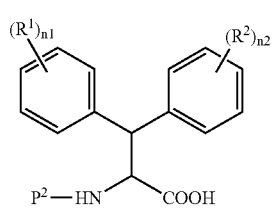

(4)

wherein
$R^1$, $R^2$, $n^1$ and $n^2$ are as defined above, and
$P^2$ is a hydrogen atom or an amino-protecting group
except a group represented by the following formula (5):

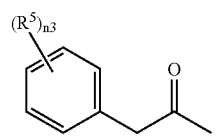

(5)

wherein $R^5$ and $n^3$ are as defined above, or a salt thereof, to a substituted phenylacetyl group represented by the above-mentioned the formula (5).

[13] A method of producing an L-diphenylalanine compound represented by the following formula (7a):

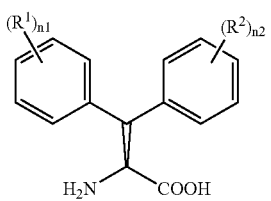

(7a)

wherein
$R^1$ and $R^2$ are each independently a halogen atom, an alkyl group, an alkoxy group, an amino group, a nitro group or a hydroxyl group, and
$n^1$ and $n^2$ are each independently an integer of 0-5, or a salt thereof, and a D-acyl-substituted diphenylalanine compound represented by the following formula (6b):

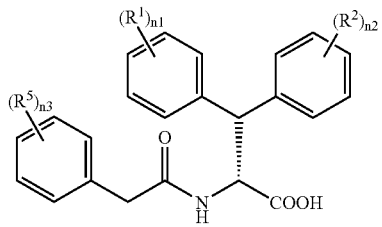
(6b)

wherein $R^1$, $R^2$, $n^1$ and $n^2$ are as defined above, $R^5$ is a halogen atom, an alkyl group, an alkoxy group, an amino group, a nitro group or a hydroxyl group, and $n^3$ is an integer of 0-5, or a salt thereof, which comprises reacting an acyl-substituted diphenylalanine compound represented by the following formula (6):

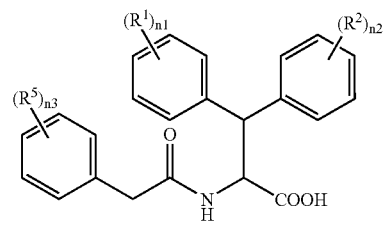
(6)

wherein each symbol is as defined above, or a salt thereof, with a penicillin amidase.

[14] A method of producing an optically active diphenylalanine compound represented by the following formulas (7a) and (6b) or a salt thereof, which comprises the following Steps (a), (b), (c) and (d);

Step (a): reacting a diphenylmethylene halide compound represented by the following formula (1):

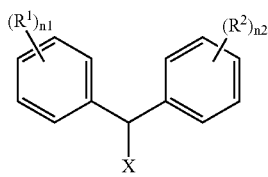
(1)

wherein $R^1$ and $R^2$ are each independently a halogen atom, an alkyl group, an alkoxy group, an amino group, a nitro group or a hydroxyl group, $n^1$ and $n^2$ are each independently an integer of 0-5, and X is a chlorine atom, a bromine atom or an iodine atom, with a malonic acid diester compound represented by the following formula (2):

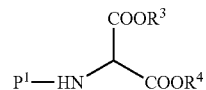
(2)

wherein $R^3$ and $R^4$ are each independently an alkyl group or an aralkyl group, or $R^3$ and $R^4$ in combination form an alkylene group, and $P^1$ is an amino-protecting group, in an organic solvent selected from N-methyl-2-pyrrolidone, N-ethyl-2-pyrrolidone and N,N-dimethylformamide, in the presence of a base selected from an alkali metal hydride and an alkali metal t-butoxide, to give a diester compound represented by the following formula (3):

(3)

wherein each symbol is as defined above;

Step (b): subjecting the diester compound to hydrolysis and decarboxylation, to give a diphenylalanine compound represented by the following formula (4):

(4)

wherein $R^1$, $R^2$, $n^1$ and $n^2$ are as defined above, and $P^2$ is a hydrogen atom or an amino-protecting group, or a salt thereof;

Step (c): converting $P^2$ of the diphenylalanine compound except a compound wherein $P^2$ is a group represented by the following formula (5):

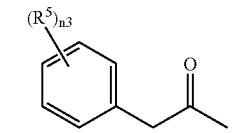
(5)

wherein
R⁵ is a halogen atom, an alkyl group, an alkoxy group, an amino group, a nitro group or a hydroxyl group, and
n³ is an integer of 0-5, or a salt thereof, to a substituted phenylacetyl group represented by the above-mentioned the formula (5), to give an acyl-substituted diphenylalanine compound represented by the following formula (6):

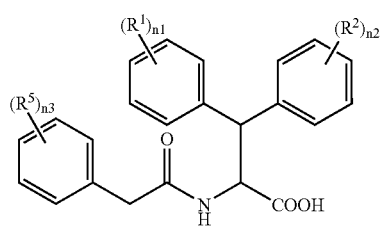

(6)

wherein each symbol is as defined above, or a salt thereof; and

Step (d): reacting the acyl-substituted diphenylalanine compound or a salt thereof with a penicillin amidase to give an L-diphenylalanine compound represented by the following formula (7a):

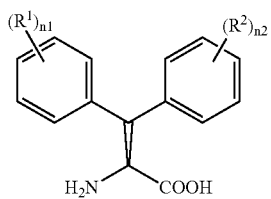

(7a)

wherein each symbol is as defined above, or a salt thereof, and a D-acyl-substituted diphenylalanine compound represented by the following formula (6b):

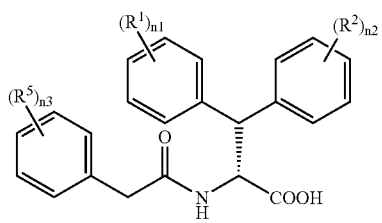

(6b)

wherein each symbol is as defined above, or a salt thereof.

[15] A method of producing an L-N-protected phenylalanine compound represented by the following formula (8a):

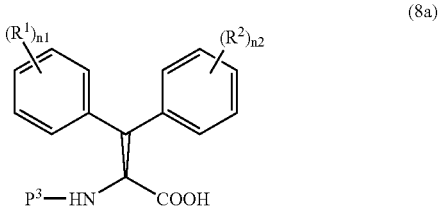

(8a)

wherein
R¹ and R² are each independently a halogen atom, an alkyl group, an alkoxy group, an amino group, a nitro group or a hydroxyl group,
$n^1$ and $n^2$ are each independently an integer of 0-5, and
$P^3$ is an amino-protecting group, or a salt thereof, which comprises obtaining an L-diphenylalanine compound represented by the following formula (7a):

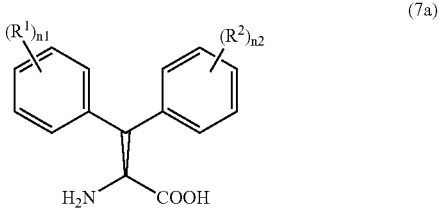

(7a)

wherein each symbol is as defined above, or a salt thereof, according to the method of the above-mentioned [13]; and protecting the amino group of the L-diphenylalanine compound or a salt thereof.

[16] The method of above-mentioned [15], wherein $P^3$ is a tert-butoxycarbonyl group.

[17] A method of producing a D-diphenylalanine compound represented by the following formula (7b):

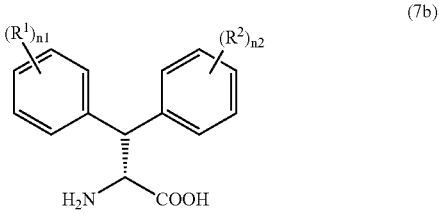

(7b)

wherein
R¹ and R² are each independently a halogen atom, an alkyl group, an alkoxy group, an amino group, a nitro group or a hydroxyl group, and
$n^1$ and $n^2$ are each independently an integer of 0-5, or a salt thereof, which comprises obtaining a D-acyl-substituted diphenylalanine compound represented by the following formula (6b):

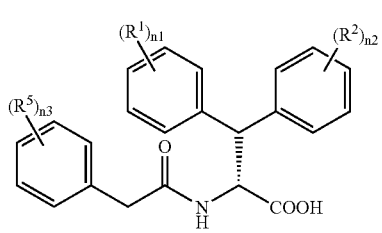

(6b)

wherein $R^1$, $R^2$, $n^1$ and $n^2$ are as defined above, $R^5$ is a halogen atom, an alkyl group, an alkoxy group, an amino group, a nitro group or a hydroxyl group, and $n^3$ is an integer of 0-5, or a salt thereof, according to the method of the above-mentioned [13]; and subjecting the D-acyl-substituted diphenylalanine compound or a salt thereof to deacylation.

[18] A method of producing a D-N-protected diphenylalanine compound represented by the following formula (8b):

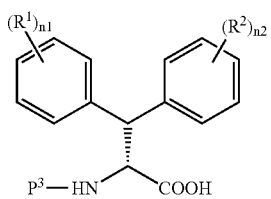

(8b)

wherein $R^1$ and $R^2$ are each independently a halogen atom, an alkyl group, an alkoxy group, an amino group, a nitro group or a hydroxyl group, $n^1$ and $n^2$ are each independently an integer of 0-5, and $P^3$ is an amino-protecting group, or a salt thereof, which comprises obtaining a D-diphenylalanine compound represented by the following formula (7b):

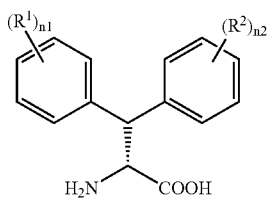

(7b)

wherein each symbol is as defined above, or a salt thereof, according to the method of the above-mentioned [17], and protecting the amino group of the D-diphenylalanine compound or a salt thereof.

[19] The method of above-mentioned [18], wherein $p^3$ is a tert-butoxycarbonyl group.

[20] An acyl-substituted diphenylalanine compound represented by the following formula (6):

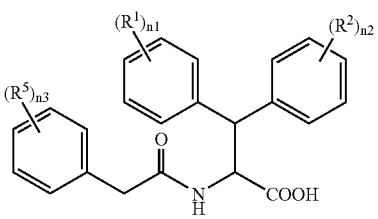

(6)

wherein $R^1$, $R^2$ and $R^5$ are each independently a halogen atom, an alkyl group, an alkoxy group, an amino group, a nitro group or a hydroxyl group, and $n^1$, $n^2$ and $n^3$ are each independently an integer of 0-5, or a salt thereof.

[21] A crystal of racemic N-acetyldiphenylalanine, which shows an X-ray diffraction pattern having characteristic peaks at diffraction angles 2θ of 5.8°, 11.5°, 21.6°, 23.2° and 28.7° obtained by powder X-ray diffraction analysis using Cu—Kα ray.

[22] The crystal of above-mentioned [21], which is obtained by adding a poor solvent to a solution of racemic N-acetyldiphenylalanine in acetate.

[23] A crystal of racemic N-acetylbis(4-fluorophenyl)alanine, which shows an X-ray diffraction pattern having characteristic peaks at diffraction angles 2θ of 17.1°, 21.8°, 22.0°, 22.7°, 23.1° and 25.4° by powder X-ray diffraction analysis using Cu—Kα ray.

[24] A crystal of racemic N-acetylbis(4-fluorophenyl)alanine, is which shows an X-ray diffraction pattern having characteristic peaks at diffraction angles 2θ of 12.8°, 17.6°, 19.2° and 24.3° by powder X-ray diffraction analysis using Cu—Kα ray.

[25] The crystal of above-mentioned [23], which is obtained by adding a poor solvent to a solution of racemic N-acetylbis(4-fluorophenyl)alanine in acetate.

[26] The crystal of above-mentioned [24], which is obtained by cooling a solution of racemic N-acetylbis(4-fluorophenyl)alanine in acetate.

According to the present invention, a novel diphenylalanine compound or a salt thereof, which is capable of substrate-specifically reacting with a penicillin amidase is provided. In addition, the diphenylalanine compound or a salt thereof and the optically active diphenylalanine compound or a salt thereof can be conveniently produced in a high yield. Moreover, racemic N-acetyldiphenylalanine and racemic N-acetylbis(4-fluorophenyl)alanine can be obtained at a high purity in the form of crystals convenient for preservation and transportation.

BEST MODE FOR EMBODYING THE INVENTION

Figure 1:
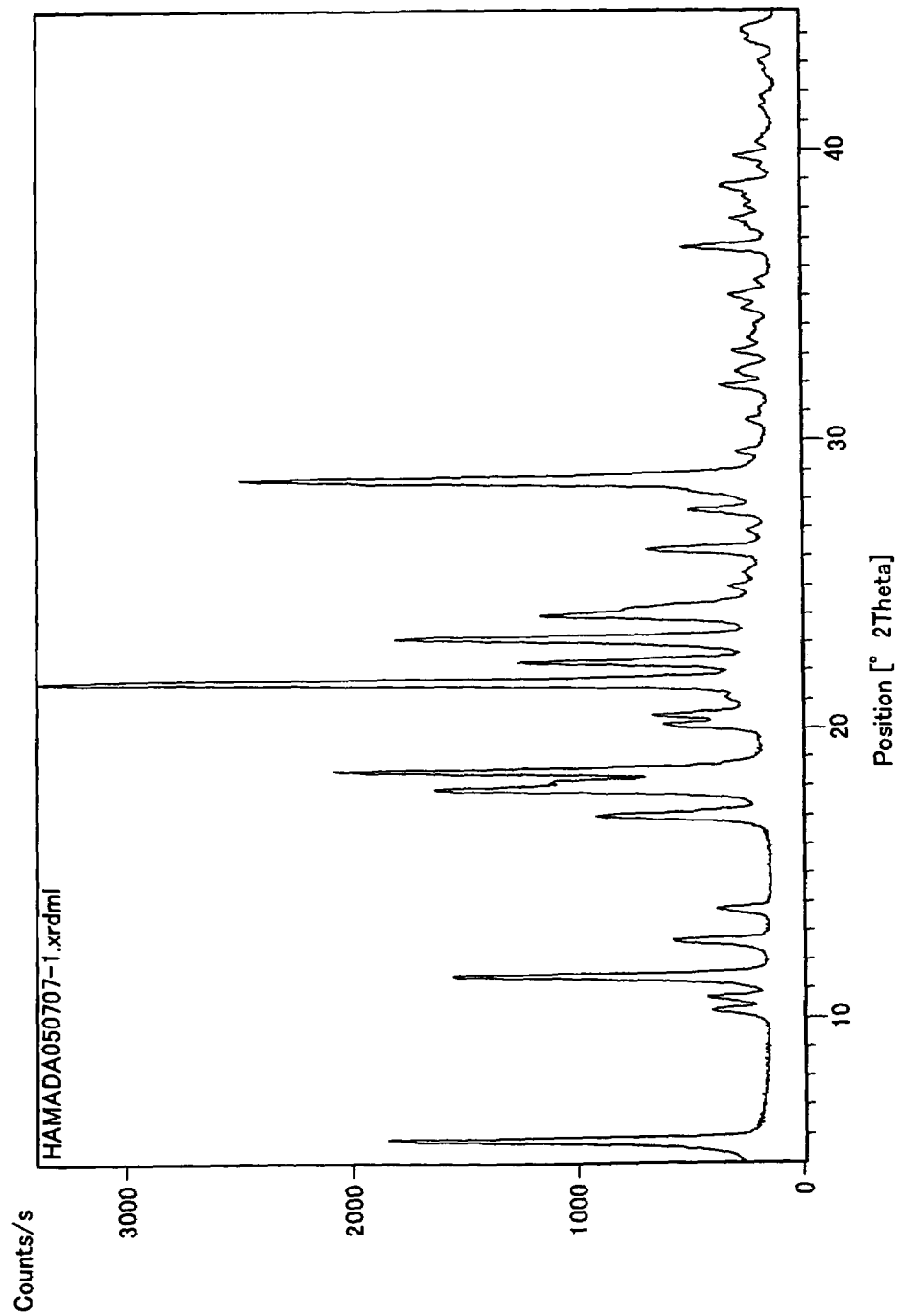
FIG. 1 is a powder X-ray diffraction chart of the dry crystal of racemic N-acetyldiphenylalanine in Example 7, wherein the vertical axis shows diffraction intensity and the axis of abscissas shows diffraction angles 2θ [deg].

The present invention is described in detail in the following.

The definitions of the symbols used in the respective formulas in the present specification are first explained.

As the halogen atom for $R^1$, $R^2$ or $R^5$, a chlorine atom, a bromine atom, a fluorine atom are preferable, and a fluorine atom is more preferable.

As the alkyl group for $R^1$, $R^2$, $R^3$, $R^4$ or $R^5$, a linear or branched alkyl group having preferably 1-10 carbons, more preferably 1-7 carbons, still more preferably 1-4 carbons, is preferable. To be specific, methyl group, ethyl group, propyl group, isopropyl group, butyl group, isobutyl group, sec-butyl group, tert-butyl group, pentyl group, hexyl group, heptyl group, octyl group and the like can be mentioned. Of these, methyl group, ethyl group, propyl group, isopropyl group, butyl group, tert-butyl group and the like are preferable. The alkyl group is optionally substituted by one or more substituents such as a halogen atom (e.g., chlorine atom, bromine atom, fluorine atom), a hydroxyl group, an alkoxy group having 1-6 carbons (e.g., methoxy group) and the like.

As the alkoxy group for $R^1$, $R^2$ or $R^5$, a linear or branched alkoxy group having preferably 1-10 carbons, more preferably 1-7 carbons, still more preferably 1-4 carbons, is preferable. To be specific, methoxy group, ethoxy group, propoxy group, isopropoxy group, butoxy group, isobutoxy group, sec-butoxy group, tert-butoxy group, pentyloxy group, hexyloxy group, heptyloxy group, octyloxy group and the like can be mentioned. Of these, methoxy group, ethoxy group, propoxy group, isopropoxy group, butoxy group, tert-butoxy group and the like are preferable. The alkoxy group is optionally substituted by one or more substituents such as a halogen atom (e.g., chlorine atom, bromine atom, fluorine atom), a hydroxyl group, an alkoxy group, having 1-6 carbons (e.g., methoxy group) and the like.

The amino group for $R^1$, $R^2$ or $R^5$ is optionally mono- or di-substituted by the aforementioned alkyl group, aryl group or aralkyl group, or optionally protected by a group exemplified for the below-mentioned amino-protecting group for $P^1$, $P^2$ or $P^3$.

The hydroxyl group for $R^1$, $R^2$ or $R^5$ is optionally protected, and as the protecting group, conventionally known ones can be mentioned. To be specific, benzyl group, trimethylsilyl group, triethylsilyl group, tert-butyldimethylsilyl group and the like can be mentioned.

$R^1$ in the number of $n^1$ may be the same or different, and $R^2$ in the number of $n^2$ and $R^5$ in the number of $n^3$ may similarly be the same or different.

The aralkyl group for $R^3$ or $R^4$ means an alkyl group substituted by an aryl group. The alkyl moiety has preferably 1-6 carbons, more preferably 1-3 carbons. To be specific, methyl group, ethyl group, propyl group, isopropyl group and the like can be mentioned. The aryl moiety has preferably 6-14 (more preferably 6-8) carbons. To be specific, phenyl group, naphthyl group and the like can be mentioned. The total carbon number of the aralkyl group is preferably 7-20, more preferably 7-11. To be specific, benzyl group, 1-phenylethyl group, 2-phenylethyl group and the like can be mentioned. Of these, benzyl group is preferable. The aralkyl group is optionally substituted by one or more substituents such as a halogen atom (e.g., chlorine atom, bromine atom, fluorine atom), a hydroxyl group, an alkyl group having 1-6 carbons (e.g., methyl group), an alkoxy group having 1-6 carbons (e.g., methoxy group), a haloalkyl group (e.g., trifluoromethyl group), a haloalkoxy group (e.g., trifluoromethoxy group) and the like.

As the alkylene group which $R^3$ and $R^4$ in combination form, a linear or branched alkylene group having preferably 2-6 carbons, more preferably 2-4 carbons, can be mentioned. To be specific, ethylene group, trimethylene group, propylene group and tetramethylene group can be mentioned. Of these, trimethylene group and tetramethylene group are preferable.

As the amino-protecting group for $P^1$, $P^2$ or $P^3$, the groups described in Protecting Groups in Organic Chemistry 2nd edition (John Wiley & Sons, Inc. 1991) can be mentioned. To be specific, an acyl group, an alkyl group, an aralkyl group, a silyl group and the like can be mentioned. As the acyl group, for example, a formyl group, a $C_{1-6}$ alkyl-carbonyl group (e.g., acetyl group), a $C_{6-8}$ aryl-carbonyl group, a $C_{7-11}$ aralkyl-carbonyl group (e.g., phenylacetyl group) and the like can be mentioned. As the alkyl group, for example, those similar to the alkyl group for $R^1$, $R^2$, $R^3$, $R^4$ or $R^5$ can be mentioned. As the aralkyl group, those similar to the aralkyl group for $R^3$ or $R^4$ can be mentioned. As the silyl group, for example, a trialkyl-substituted silyl group such as trimethylsilyl group, triethylsilyl group, tert-butyldimethylsilyl group and the like can be mentioned. The alkyl moiety has preferably 1-4 carbons, and to be specific, methoxy group, ethoxy group, propoxy group, isopropoxy group, butoxy group, tert-butoxy group and the like can be mentioned. In addition, methoxymethyl group, methylthiomethyl group, benzyloxymethyl group, methoxyethoxymethyl group, tetrahydropyranyl group, methoxycarbonyl group (Moc group), 9-fluorenylmethoxycarbonyl group (Fmoc group), 2,2,2-trichloroethoxycarbonyl group, benzyloxycarbonyl group (Cbz group), tert-butoxycarbonyl group (Boc group) and the like can also be mentioned.

Particularly preferable embodiment of each symbol is as shown below.

$R^1$ and $R^2$ are each preferably a halogen atom or an alkyl group having 1-10 carbons, more preferably a halogen atom, particularly preferably a fluorine atom. $R^1$ and $R^2$ may be the same or different.

$R^3$ and $R^4$ are each preferably an alkyl group having 1-10 carbons, more preferably an alkyl group having 1-4 carbons, particularly preferable an ethyl group. $R^3$ and $R^4$ may be the same or different.

$R^5$ is preferably a halogen atom or an alkyl group having 1-10 carbons.

$P^1$ is preferably an acyl group having 1-7 carbons, particularly preferably an acetyl group or a phenylacetyl group.

$P^2$ is preferably a hydrogen atom or an acyl group having 1-7 carbons, particularly preferably a hydrogen atom, an acetyl group or a phenylacetyl group.

$P^3$ is preferably a Moc group, a Fmoc group, a Cbz group or a Boc group, particularly preferably a Boc group.

X is preferably a chlorine atom or a bromine atom.

Preferably, $n^1$, $n^2$ and $n^3$ are each independently 0, 1 or 2. Particularly preferably, $n^1$ and $n^2$ are each independently 0 or 1, and $n^3$ is 0.

Now, the production method of the present invention is explained below. The production method of the present invention is shown in the following reaction scheme.
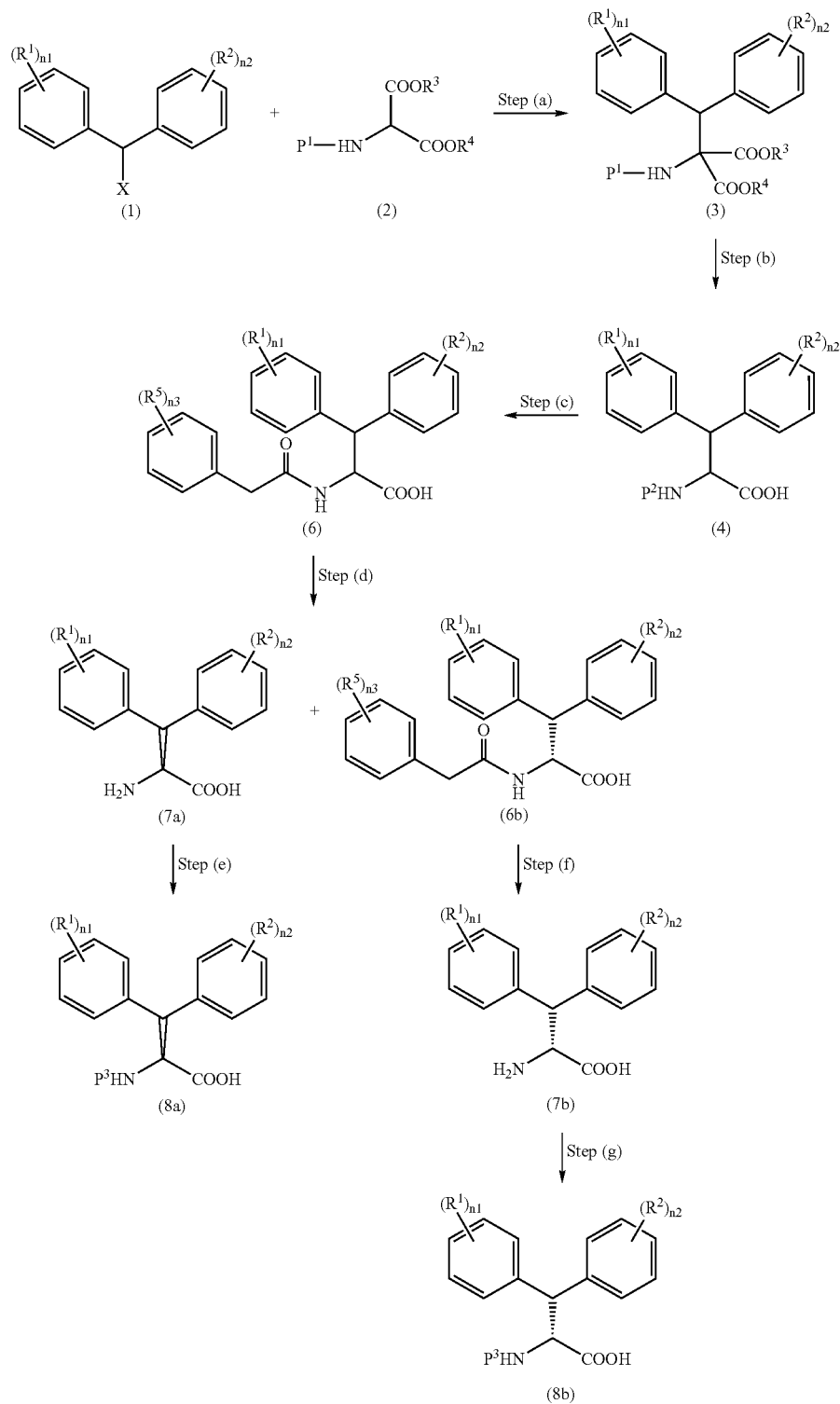
wherein each symbol is as defined above.

Step (a)

Step (a) is a step for obtaining a diester compound represented by the formula (3) (hereinafter to be also referred to as "compound (3)") by reacting a diphenylmethylene halide compound represented by the formula (1) (hereinafter to be also referred to as "compound (1)") with a malonic acid diester compound represented by the formula (2) (hereinafter to be also referred to as "compound (2)") in an organic solvent selected from N-methyl-2-pyrrolidone, N-ethyl-2-pyrrolidone and N,N-dimethylformamide, in the presence of a base selected from an alkali metal hydride and an alkali metal t-butoxide.

The reaction in Step (a) is carried out in the presence of a base selected from an alkali metal hydride and an alkali metal t-butoxide. As used herein, as the alkali metal hydride, for example, lithium hydride, potassium hydride, sodium hydride and the like can be mentioned. Of these, sodium hydride and potassium hydride are preferable, and sodium hydride is particularly preferable. As the alkali metal t-butoxide, sodium t-butoxide, potassium t-butoxide and the like can be mentioned. Of these, potassium t-butoxide is particularly preferable. The amount of the base to be used is generally 1-1.5 equivalents, preferably 1.1-1.3 equivalents, relative to compound (2).

The above-mentioned reaction can be also carried out in the co-presence of an iodine compound or bromine compound, for the purpose of promoting the reaction. In this case, when X is a chlorine atom, the reaction is carried out in the co-presence of an iodine compound and/or a bromine compound, preferably an iodine compound. When X is a bromine atom, the reaction is carried out in the co-presence of an iodine compound.

As the iodine compound, metal iodides and quaternary ammonium iodides can be preferably used. As the metal iodide, alkali metal iodides are preferable and, for example, lithium iodide, potassium iodide, sodium iodide and the like can be mentioned. Of these, potassium iodide and sodium iodide are particularly preferable. As the quaternary ammonium iodide, for example, tetrabutylammonium iodide, tetraheptylammonium iodide and the like can be mentioned. Of these, tetrabutylammonium iodide is particularly preferable. As the bromide compound, metal bromides and quaternary ammonium bromides can be preferably used. As the metal bromide, alkali metal bromides are preferable and, for example, lithium bromide, potassium bromide, sodium bromide and the like can be mentioned. Of these, potassium bromide and sodium bromide are particularly preferable. As the quaternary ammonium bromide, for example, tetrabutylammonium bromide, tetraheptylammonium bromide and the like can be mentioned. Of these, tetrabutylammonium bromide is particularly preferable. The amount of the iodine compound or bromine compound to be used is generally 0.05-1.0 equivalent, preferably 0.5-1.0 equivalent, relative to compound (1).

The reaction in Step (a) is carried out in an organic solvent selected from N-methyl-2-pyrrolidone (aka: N-methylpyrrolidinone and 1-methylpyrrolidinone), N-ethyl-2-pyrrolidone and N,N-dimethylformamide. From the aspect of improved yield, N-methyl-2-pyrrolidone and N-ethyl-2-pyrrolidone are preferable, and N-methyl-2-pyrrolidone is particularly preferable. Two or more of N-methyl-2-pyrrolidone, N-ethyl-2-pyrrolidone and N,N-dimethylformamide can be mixed at an appropriate ratio and used. As long as the effect of this reaction is exhibited, a solvent besides N-methyl-2-pyrrolidone, N-ethyl-2-pyrrolidone and N,N-dimethylformamide can be used. As such solvent, aprotic organic solvents are preferably used and, for example, dimethyl sulfoxide, hexamethylphosphoric triamide, acetonitrile, toluene and the like can be mentioned. The amount of the organic solvent to be used can be appropriately determined depending on the kind of the compound. It is generally 3- to 20-fold weight, preferably 5- to 10-fold weight, relative to compound (1).

The amount of compound (2) to be used is generally 1-1.5 equivalents, preferably 1.1-1.3 equivalents, relative to compound (1). When the amount of compound (2) to be used is smaller than the above-mentioned range, the reaction tends to be insufficient.

For reaction conditions, when the base is an alkali metal hydride, the reaction temperature is generally 30-60° C., preferably 40-50° C., and the reaction time is generally 1-16 hrs, preferably 3-6 hrs. When the base is an alkali metal t-butoxide, the reaction temperature is generally 30-80° C., preferably 60-70° C., and the reaction time is generally 3-24 hrs, preferably 3-8 hrs.

After the completion of the reaction, an organic solvent (e.g., hydrocarbons such as toluene etc.) and water are added to the reaction mixture, and the mixture is partitioned. Then, the obtained organic layer is washed with water and the like, and concentrated to give compound (3). Alternatively, after the completion of the reaction, Step (b) can also be performed sequentially in the same reaction container, without the above-mentioned work-up.

Step (b)

Step (b) is a step for obtaining a diphenylalanine compound represented by the formula (4) or a salt thereof (hereinafter to be also referred to as "compound (4)") by subjecting compound (3) to hydrolysis and decarboxylation, whereby compound (4) can be conveniently obtained in a high yield.

The hydrolysis and decarboxylation can be carried out according to known methods and, for example, a method comprising reacting compound (3) with a base (e.g., sodium hydroxide) in an alcohol (e.g., ethanol) or in a mixed solvent of an alcohol and water can be mentioned. The above-mentioned reaction is generally carried out at a temperature within the range of from 80° C. to the refluxing temperature of the solvent to be used (preferably 85-90° C.), and the reaction time is generally 1-16 hrs, preferably 3-6 hrs. After the completion of the reaction, an organic solvent (e.g., hydrocarbons such as toluene etc.) and water are added to the reaction mixture, and the mixture is partitioned. Then, an acetate (e.g., ethyl acetate, isopropyl acetate) and water are added to the obtained aqueous layer, and the mixture is acidified (generally pH 0.5-3, preferably pH 1-2) with an acid (e.g., hydrochloric acid, sulfuric acid) and extracted. The obtained organic layer is washed with water and the like, and concentrated to give compound (4).

Step (a) and Step (b) can also be performed sequentially in the same reaction container. For example, a method comprising reacting the reaction mixture with a base (e.g., sodium hydroxide, potassium hydroxide) after the completion of the reaction of Step (a) can be mentioned. The reaction is generally carried out at a temperature within the range of from 50° C. to the refluxing temperature of the solvent to be used (preferably 60-70° C.), and the reaction time is generally 1-16 hrs, preferably 3-6 hrs.

After the completion of the reaction, the reaction mixture is partitioned. The obtained aqueous layer is neutralized (generally pH 6-8, preferably pH 7-8) with an acid (e.g., hydrochloric acid, sulfuric acid), and an acetate (e.g., ethyl acetate, isopropyl acetate) is added. Then the mixture is acidified (generally pH 0.5-3, preferably pH 1-2) with an acid (e.g., hydrochloric acid, sulfuric acid) and extracted. The obtained organic layer is washed successively with an acid (e.g., hydrochloric acid) and saturated brine, and concentrated to give compound (4).

While the property of compound (4) obtained by concentration is amorphous, compound (4) can also be obtained as a crystal by ceasing concentration on the way and cooling the acetate solution (e.g., ethyl acetate, isopropyl acetate) as it is, or adding a particular poor solvent (e.g., toluene) to the acetate solution (e.g., ethyl acetate, isopropyl acetate) to allow crystal precipitation.

For example, a crystal of racemic N-acetyldiphenylalanine (aka, 2-acetylamino-3,3-diphenylpropanoic acid) is obtained by a crystal precipitation method comprising adding toluene as a poor solvent to the acetate (e.g., ethyl acetate, isopropyl acetate) solution. The crystal has a powder X-ray diffraction pattern having characteristic peaks at diffraction angles 2θ of 5.8°, 11.5°, 21.6°, 23.2° and 28.7° by powder X-ray diffraction analysis using Cu—Kα ray.

As to the crystal of racemic N-acetylbis(4-fluorophenyl)alanine (aka, 2-acetylamino-3,3-bis(4-fluorophenyl)propanoic acid), it has been clarified that there are two kinds of crystals due to different crystal precipitation methods.

For example, a crystal of racemic N-acetylbis(4-fluorophenyl)alanine obtained by a crystal precipitation method comprising adding toluene as a poor solvent to the acetate (e.g., ethyl acetate, isopropyl acetate) solution has a powder X-ray diffraction pattern having characteristic peaks at diffraction angles 2θ of 17.1°, 21.8°, 22.0°, 22.7°, 23.1° and 25.4° by powder X-ray diffraction analysis using Cu—Kα ray.

In addition, a crystal of racemic N-acetylbis(4-fluorophenyl)alanine obtained by a crystal precipitation method comprising cooling the acetate (e.g., ethyl acetate, isopropyl acetate) solution has a powder X-ray diffraction pattern having characteristic peaks at diffraction angles 2θ of 12.8°, 17.6°, 19.2° and 24.3° by powder X-ray diffraction analysis using Cu—Kα ray.

In this manner, racemic N-acetyldiphenylalanine and racemic N-acetylbis(4-fluorophenyl)alanine can be obtained at a high purity as crystals convenient for preservation and transportation.

It is evident that diffraction angles (2θ) in powder X-ray diffraction spectrum may have a measurement error of about ±0.2 degree, and such error does not deny the homology of crystals.

Step (c)

Step (c) is a step for obtaining an acyl-substituted diphenylalanine compound represented by the formula (6) or a salt thereof (hereinafter to be also referred to as "compound (6)") by converting $P^2$ comprising compound (4) to a substituted phenylacetyl group.

That is, as shown in the following reaction scheme, of compound (4), a compound wherein $P^2$ is other than a group represented by the formula (5):

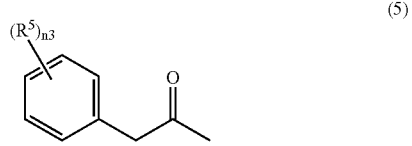

wherein each symbol is as defined above, is subjected to amino-deprotection (a compound wherein $P^2$ is hydrogen atom is not necessary) to give a compound represented by the formula (4c) or a salt thereof (hereinafter to be also referred to as "compound (4c)"), and then compound (4c) is reacted with an acyl halide represented by the formula (5c) (hereinafter to be also referred to as "compound (5c)") to introduce a substituted phenylacetyl group represented by the above-mentioned formula (5), whereby compound (6) can be conveniently obtained in a high yield:

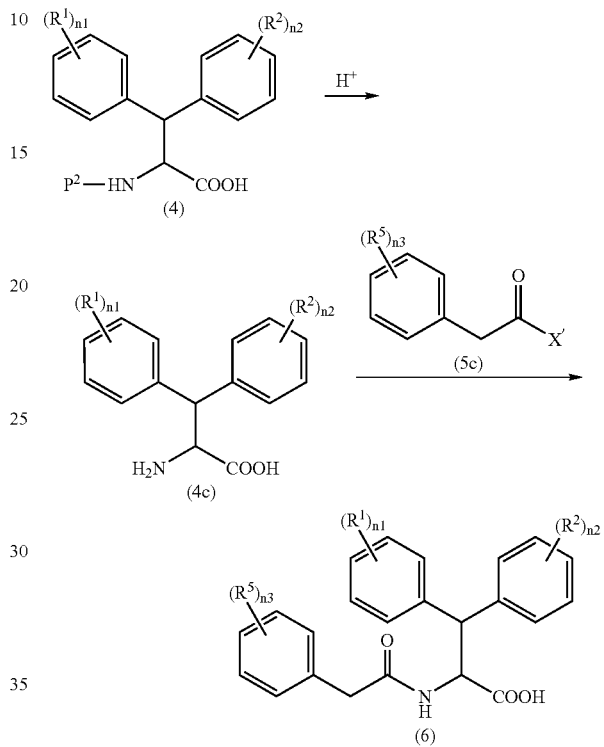

wherein X' is a chlorine atom, a bromine atom or an iodine atom, and other symbols are as defined above.

The amino-deprotection of compound (4) can be carried out by a known method and, for example, acid treatment, catalytic reduction and the like can be mentioned.

For example, the acid treatment can be carried out by reacting compound (4) with an acid (e.g., hydrochloric acid, sulfuric acid) generally at 80-100° C. (preferably 90-100° C.), generally for 1-16 hrs (preferably 3-6 hrs). Here, compound (4c) can be obtained as an acid addition salt.

The catalytic reduction can be carried out by a known method, for example, introducing hydrogen to compound (4) in the presence of a reduction catalyst such as palladium carbon and the like.

Then, compound (4c) is reacted with compound (5c) under basic conditions (generally pH 10-13, preferably 11-12), whereby compound (6) can be obtained in a high yield. As the base, sodium hydroxide, potassium hydroxide and the like can be mentioned. When the amount of compound (5c) to be used is generally 1-1.2 equivalents, preferably 1.05-1.1 equivalents, relative to compound (4). The amount of compound (5c) to be used is smaller than the above-mentioned range, the reaction tends to be insufficient. The reaction temperature is generally 0-40° C., preferably 20-30° C. The reaction time is generally 1-5 hrs, preferably 2-3 hrs.

After the completion of reaction, an acetate (e.g., ethyl acetate) is added to the reaction mixture, and the mixture is acidified (generally pH 0.5-3, preferably pH 1-2) with an acid (e.g., hydrochloric acid, sulfuric acid) and partitioned. The obtained organic layer is concentrated, or a solvent for crystal precipitation (e.g., hydrocarbon such as hexane etc.) is added to the obtained organic layer to allow crystal precipitation, whereby compound (6) can be obtained.

Of compound (4), a compound wherein $P^2$ is a group represented by the formula (5) can be subjected to the below-mentioned Step (d) after the completion of Step (b), without applying Step (c).

Step (d)

Step (d) is a step for obtaining an L-diphenylalanine compound represented by the formula (7a) or a salt thereof (hereinafter to be also referred to as "compound (7a)") and a D-acyl-substituted diphenylalanine compound represented by the formula (6b) or a salt thereof (hereinafter to be also referred to as "compound (6b)") by reacting racemic compound (6) with a penicillin amidase. The penicillin amidase acts on compound (6) in a substrate-specific manner, whereby an L-form, i.e., a compound represented by the formula (6a) (hereinafter to be also referred to as "compound (6a)") is subjected to deacylation by hydrolysis to produce compound (7a), but a D-form, i.e., compound (6b) is hardly hydrolyzed.

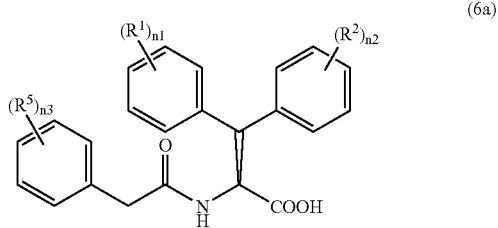

(6a)

wherein each symbol is as defined above.

As the penicillin amidase, any can be used without particular limitation as long as it is an enzyme classified as E.C.3.5.1.11 produced from microorganisms such as bacteria, *actinomyces*, fungi and the like. As such microorganisms, for example, *Acetobactor, Xanthomonas, Mycoplana, Protaminobacter, Aeromonas, Pseudomonas, Flavobacteriu M, Aphanocladiu M, Cephalosporiu M, Acetobacter pasteurianu M, Bacillus megateriu M, Xanthomonas citrii, Kluyvera citrophila*, and *Escherichia coli* can be mentioned. The penicillin amidase can be used as a liberated water-soluble enzyme or water-insoluble immobilized enzyme.

The above-mentioned reaction is carried out, for example, by adding a penicillin amidase to compound (6) under basic conditions (generally pH 6.8-8.5, preferably pH 7.2-7.9) generally at 30-40° C. (preferably 36-38° C.), generally for 2-48 hrs (preferably 8-24 hrs). As the base, sodium hydroxide, potassium hydroxide and the like can be mentioned.

The substrate concentration of compound (6) is generally 0.01-0.2 mol/L (preferably 0.02-0.1 mol/L). The concentration of the penicillin amidase is generally 10-1000 U/mL (preferably 10-100 U/mL). The above-mentioned reaction can also be carried out by using a conventionally employed buffer such as phosphate buffer and the like.

After the completion of the reaction, compound (7a) is separated from compound (6b). To be specific, an organic solvent (e.g., acetate such as ethyl acetate and the like) is added to the reaction mixture and the mixture is acidified (generally pH 0.5-2.0, preferably pH 1.0-2.0) with an acid (e.g., hydrochloric acid, sulfuric acid), and partitioned. Then, compound (7a) is isolated from the aqueous layer, and compound (6b) is isolated from the organic layer. Furthermore, they can be purified by, where necessary, applying recrystallization. Alternatively, the aqueous layer obtained by extraction may be directly used for the below-mentioned Step (e).

When an immobilized enzyme is used, for example, the immobilized penicillin amidase is removed by filtration after the completion of reaction, and compound (7a) and compound (6b) can be obtained by similar operation as in the above. The immobilized penicillin amidase can be re-used after washing with water and the like.

By such method, compound (7a) which is useful as an intermediate for pharmaceutical products such as anti-HIV drugs, dipeptidyl peptidase inhibitors and the like can be conveniently obtained in a high yield.

Step (e)

Step (e) is a step for obtaining an L-N-protected phenylalanine compound represented by the formula (8a) or a salt thereof (hereinafter to be also referred to as "compound (8a)") by protecting the amino group of compound (7a). Step (e) can be performed by a known method, for example, the method described in Protecting Groups in Organic Chemistry 2nd edition (John Wiley & Sons, Inc. 1991).

As a preferably embodiment of Step (e), protection of the amino group using a Boc group is explained in the following. For protection of the amino group using a Boc group, for example, an aqueous solution of compound (7a) obtained in Step (d) (the aqueous layer obtained by the extraction operation in Step (d) may be directly used) is basified (generally pH 7-9, preferably pH 8), alcohol (e.g., methanol) and di-t-butyl dicarbonate are added to the aqueous solution, and the mixture is allowed to react generally at 0-50° C. (preferably 20-40° C.), generally for 1-24 hrs (preferably 1-6 hrs). As the base, for example, potassium hydrogencarbonate and the like can be used. The amount of di-t-butyl dicarbonate to be used is generally 1-1.2 equivalents (preferably 1.05-1.1 equivalents) relative to compound (7a). The amount of the alcohol to be used is generally 2- to 100-fold weight (preferably 5- to 20-fold weight) relative to compound (7a). After the completion of the reaction, the reaction mixture is acidified (generally pH 0.5-3, preferably pH 1-2) with an acid (e.g., hydrochloric acid, sulfuric acid) and partitioned. The obtained organic layer is washed with water and concentrated to give compound (8a). Where necessary, moreover, compound (8a) may be purified by applying crystal precipitation or column chromatography. As a result, compound (8a) useful as an intermediate for pharmaceutical products such as anti-HIV drugs, dipeptidyl peptidase inhibitors and the like can be conveniently obtained in a high yield. Furthermore, since compound (8a) is a crystal, it shows high purity and is also superior in handling property in terms of preservation, transportation and the like.

Step (f)

Step (f) is a step for obtaining a D-diphenylalanine compound represented by the formula (7b) or a salt thereof (hereinafter to be also referred to as "compound (7b)") by subjecting compound (6b) to deacylation. The deacylation can be carried out by a method similar to the acid treatment for deprotection of the amino group as described in Step (c).

Step (g)

Step (g) is a step for obtaining a D-N-protected diphenylalanine compound represented by the formula (8b) or a salt thereof (hereinafter to be also referred to as "compound (8b)") by protecting the amino group of compound (7b). Step (g) is performed by introducing an amino-protecting group by a method similar to that in Step (e), whereby optically active compound (8b) can be conveniently obtained in a high yield.

In each Step, compound (4), compound (4c), compound (6), compound (6a), compound (6b), compound (7a), compound (7b), compound (8a) and compound (8b) can be in the form of salts. When compound (1), compound (2), compound (3) and compound (5c) have an amino group as a substituent, they may be in the form of salts. As the acid addition salt, for example, salts with inorganic acids (e.g., hydrochloric acid, sulfuric acid), organic acids (e.g., acetic acid, trifluoroacetic acid, p-toluenesulfonic acid, methanesulfonic acid) and the like can be mentioned. As the basic salt, alkali metal salts (e.g., sodium salt, potassium salt), alkaline earth metal salts (e.g., calcium salt, magnesium salt), organic salts (e.g., triethylamine salt, dicyclohexylamine salt) and the like can be mentioned.

EXAMPLES

The present invention is explained in detail in the following by referring to Examples, which are not to be construed as limitative.

Example 1

Synthesis of 2-acetylamino-3,3-diphenylpropanoic acid

To a solution (1.25 M) of diethyl acetamidomalonate (6.79 g, 31.25 mmol) in N-methyl-2-pyrrolidone (25 mL) was added 60% sodium hydride (1.25 g, 31.25 mmol), and the mixture was stirred at room temperature for 1 hr. Diphenylmethylene chloride (4.45 mL, 25.0 mmol) and potassium iodide (4.15 g, 25 mmol) were added, and the mixture was stirred at 50° C. for 7 hrs. After completion of the reaction, toluene (75 mL) and water (31.5 mL) were added to the reaction mixture, and the mixture was partitioned. The organic layer was washed twice with water (31.5 mL) and concentrated. Ethanol (31.5 mL) and 2M aqueous sodium hydroxide solution (37.5 mL) were added to the concentrated solution, and the mixture was stirred at 80° C. for 11 hrs and allowed to cool to 25° C. Toluene (9 mL) was added and the mixture was partitioned. The aqueous layer was concentrated to a half volume and adjusted to pH 1.1 with concentrated hydrochloric acid, which resulted in the precipitation of white crystals. The crystals were collected by filtration and dried under vacuum to give the title compound (5.0 g).

Example 2

Synthesis of 2-amino-3,3-diphenylpropanoic acid hydrochloride

A solution (21 mL) of 2-acetylamino-3,3-diphenylpropanoic acid (2.83 g, 10 mmol) in concentrated hydrochloric acid was stirred at 90° C. for 5 hrs, and the reaction mixture was cooled in an ice bath to allow solid precipitation. The solid was collected by filtration and dried to give the title compound (2.65 g).

Example 3

Synthesis of 2-phenylacetylamino-3,3-diphenylpropanoic acid

An aqueous solution (14 mL) of 2-amino-3,3-diphenylpropanoic acid hydrochloride (2.0 g, 7.2 mmol) was adjusted to pH 12 with 1M aqueous sodium hydroxide solution. Phenylacetyl chloride (1.05 mL, 7.9 mmol) was added dropwise at 0-10° C. while adjusting the mixture to pH 11-12 with 1M aqueous sodium hydroxide solution, and the mixture was stirred at room temperature for 4 hrs. Ethyl acetate (40 mL) was added to the reaction mixture, and the mixture was adjusted to pH 1.1 with concentrated hydrochloric acid and partitioned. The obtained organic layer was warmed to 50° C. and hexane (30 mL) was added. The mixture was cooled in an ice bath to allow solid precipitation. The solid was collected by filtration and dried to give the title compound (2.41 g).

melting point: 173° C.

$^1$H NMR (400 MHz, DMSO-$d_6$) δ 3.26-3.34 (m, 2H), 4.33 (d, 1H, J=7.2 Hz), 5.19 (dd, 2H, J=5.6 Hz, 10.7 Hz), 6.88-7.34 (m, 15H), 8.51 (d, 1H, J=5.6 Hz)

$^{13}$C NMR (100 MHz, DMSO-$d_6$) δ 172.62, 170.00, 162.53, 141.54, 141.43, 136.45, 129.05, 128.74, 128.64, 128.53, 128.51, 128.37, 127.03, 126.81, 126.43, 55.52, 53.43, 42.13

MS (FAB), m/z 360 [M$^+$+H]

Example 4

Synthesis of L-2-amino-3,3-diphenylpropanoic acid

2-Phenylacetylamino-3,3-diphenylpropanoic acid (0.80 g, 2.2 mmol) was dissolved in phosphate buffer (pH 7.2, 80 mL), and the solution was warmed to 37° C. Penicillin amidase (1250U, manufactured by SIGMA) was added and the mixture was stirred at 37° C. for 6 hrs. HPLC analysis revealed the production of the objective compound at a conversion rate of 30.2% (92.9% ee, CHIRALPAK WH manufactured by Daicel Chemical Industries, Ltd., 2 mM aqueous copper sulfate solution:acetonitrile=6:4, 220 nm, 1.0 mL/min, rt). Ethyl acetate (100 mL) was added to the reaction mixture, and the mixture was adjusted to pH 1 with concentrated hydrochloric acid and partitioned to extract the objective compound into the aqueous layer. The aqueous layer was adjusted to pH 7 and partitioned to extract the objective compound into the organic layer, and the organic layer was concentrated to give the title compound.

Example 5

Synthesis of L-2-t-butoxycarbonylamino-3,3-diphenylpropanoic acid

An aqueous solution of L-2-amino-3,3-diphenylpropanoic acid (0.10 g, 0.28 mmol, 92.9% ee) was adjusted to pH 8-9 with sodium hydrogencarbonate. Ethyl acetate (1.0 mL) and di-t-butyl dicarbonate (0.1 g, 0.45 mmol) were added, and the mixture was stirred at 37° C. for 16 hrs. The reaction mixture was allowed to cool to room temperature, adjusted to pH 2 with 6N hydrochloric acid, and partitioned to extract the objective compound into the organic layer. The organic layer was concentrated. Heptane was added to the residue and the mixture was stirred overnight to allow crystal precipitation. The crystals were collected by filtration and dried to give the title compound (97% ee, SUMICHIRAL OA-4100, hexane:methanol:2-propanol:trifluoroacetic acid=98:1:1:0.1, 220 nm, 1.0 mL/min, rt).

Example 6

Synthesis of 2-acetylamino-3,3-diphenylpropanoic acid

To a solution (1.25 M) of diethyl acetamidomalonate (10.94 g, 50.57 mmol) in N-methyl-2-pyrrolidone (40 mL) was added potassium t-butoxide (5.90 g, 52.60 mmol), and the mixture was stirred at room temperature for 1 hr. Diphenylmethylene bromide (10.0 g, 46.46 mmol) was added, and the mixture was stirred at 70° C. for 5 hrs. After completion of the reaction, 2M aqueous sodium hydroxide solution (45 mL) was added to the reaction mixture, and the mixture was stirred at 70° C. for 3 hrs. The reaction mixture was allowed to cool to room temperature, toluene (19 mL) was added, and the mixture was partitioned. The aqueous layer was adjusted to pH 7.0 with concentrated hydrochloric acid (8.8 mL). Ethyl acetate (80 mL) was added, and then concentrated hydrochloric acid (13.0 mL) was added. The mixture was partitioned, and the aqueous layer was extracted with ethyl acetate (40 mL). The organic layers were combined, successively washed with 2M hydrochloric acid (40 mL, three times) and saturated brine (10 mL), and concentrated. Toluene (30 mL) was added to the concentrated solution and the mixture was concentrated at 50° C. Toluene (30 mL) was added again, and the mixture was stirred for 30 min and cooled to 0° C. over 5 hrs, which resulted in the precipitation of white crystals. The crystals were collected by filtration and dried under reduced pressure to give the title compound (9.18 g).

Example 7

Synthesis of 2-acetylamino-3,3-diphenylpropanoic acid

To a solution (1.25 M) of diethyl acetamidomalonate (13.33 g, 61.8 mmol) in N-methyl-2-pyrrolidone (40 mL) was added potassium t-butoxide (7.20 g, 64.3 mmol), and the mixture was stirred at room temperature for 1 hr. Diphenylmethylene chloride (10.0 g, 49.3 mmol) and potassium iodide (4.10 g, 24.7 mol) were added, and the mixture was stirred at 70° C. for 6 hrs. After completion of the reaction, 2M aqueous sodium hydroxide solution (45 mL) was added to the reaction mixture, and the mixture was stirred at 60° C. for 5 hrs. The reaction mixture was allowed to cool to room temperature and the mixture was partitioned. The aqueous layer was adjusted to pH 7.0 with concentrated hydrochloric acid (4.4 mL). Ethyl acetate (80 mL) was added, and then concentrated hydrochloric acid (6.9 mL) was added. The mixture was partitioned and the aqueous layer was extracted with ethyl acetate (40 mL). The organic layers were combined, successively washed with 2M hydrochloric acid (20 mL, three times) and saturated brine (10 mL), and concentrated. Toluene (30 mL) was added to the concentrated solution and the mixture was concentrated at 50° C. Toluene (30 mL) was added again, and the mixture was stirred for 30 min and cooled to 0° C. over 5 hrs, which resulted in the precipitation of white crystals. The crystals were collected by filtration and dried under reduced pressure to give the title compound (11.69 g). The powder X-ray (Cu—Kα ray) of the dry crystals showed characteristic peaks at 5.8°, 11.5°, 21.6°, 23.2° and 28.7°, as shown in FIG. 1.

Example 8

Synthesis of 2-acetylamino-3,3-bis(4-fluorophenyl)propanoic acid

To a solution of diethyl acetamidomalonate (22.79 g, 105.4 mmol) in N-methyl-2-pyrrolidone (84 mL) was added 55% sodium hydride (4.58 g, 105.2 mmol), and the mixture was stirred at room temperature for 1 hr. Bis(4-fluorophenyl)methylene chloride (16.5 mL, 84.7 mmol) and potassium iodide (13.95 g, 84.0 mmol) were added, and the mixture was stirred at 50° C. for 5 hrs. After completion of the reaction, toluene (200 mL) and water (100 mL) were added to the reaction mixture, and the mixture was partitioned. The obtained organic layer was washed twice with water (100 mL) and concentrated. Ethanol (108 mL) and 2M aqueous sodium hydroxide solution (127 mL) were added to the concentrated solution, and the mixture was stirred at 90° C. for 2.5 hrs. The reaction mixture was allowed to cool to 25° C., toluene (200 mL) and water (50 mL) were added, and the mixture was partitioned. The aqueous layer was concentrated to a half volume, and isopropyl acetate (60 mL) and water (130 mL) were added. The mixture was adjusted to pH 1.1 with concentrated hydrochloric acid and partitioned. The organic layer was washed with water (200 mL), concentrated and dried under vacuum to give the title compound (28.24 g).

Example 9

Synthesis of 2-amino-3,3-bis(4-fluorophenyl)propanoic acid hydrochloride

A solution (144 mL) of 2-acetylamino-3,3-bis(4-fluorophenyl)propanoic acid (25.34 g, 79.9 mmol) in concentrated hydrochloric acid was stirred at 90° C. for 5 hrs, and cooled in an ice bath to allow solid precipitation. The solid was collected by filtration and dried to give the title compound (22.79 g).

Example 10

Synthesis of 2-phenylacetylamino-3,3-bis(4-fluorophenyl)propanoic acid

An aqueous solution (188 mL) of 2-amino-3,3-bis(4-fluorophenyl)propanoic acid hydrochloride (21.50 g, 68.9 mmol) was adjusted to pH 12.2 with 1M aqueous sodium hydroxide solution (154.2 g). Phenylacetyl chloride (10.8 mL, 81.7 mmol) was added dropwise at 0-10° C. while adjusting the mixture to pH 11-12 with 1M aqueous sodium hydroxide solution, and the mixture was stirred at room temperature for 3 hrs. Ethyl acetate (400 mL) was added to the reaction mixture, and the mixture was adjusted to pH 1.1 with concentrated hydrochloric acid and partitioned. The obtained organic layer was warmed to 40° C. and hexane (525 mL) was added. The mixture was cooled in an ice bath to allow solid precipitation. The solid was collected by filtration and dried to give the title compound (21.75 g).

melting point: 187° C.

$^1$H NMR (400 MHz, DMSO-$d_6$) δ 3.25-3.35 (m, 2H), 4.35 (d, 1H, J=7.2 Hz), 5.13 (dd, 2H, J=5.6 Hz, 10.7 Hz), 6.68-7.39 (m, 13H), 8.52 (d, 1H, J=5.6 Hz)

$^{13}$C NMR (100 MHz, DMSO-$d_6$) δ 172.49, 170.04, 162.53, 160.16, 160.12, 137.57, 137.39, 136.39, 130.45, 130.38, 130.30, 129.02, 128.29, 126.47, 115.60, 115.44, 115.39, 115.23, 55.67, 51.82, 42.18

MS (FAB), m/z 396 [M$^+$+H]

Example 11

Synthesis of L-2-amino-3,3-bis(4-fluorophenyl)propanoic acid

An aqueous solution (500 ml) of 2-phenylacetylamino-3,3-diphenylpropanoic acid (5 g, 12.6 mmol) was adjusted to pH 7.8 with 0.8M aqueous potassium hydroxide solution (6 mL). Penicillin amidase (10000U, manufactured by SIGMA) was added, and the mixture was stirred at 37° C. for 24 hrs. HPLC analysis revealed the production of the objective compound at a conversion rate of 47% (88% ee, CHIRALPAK WH manufactured by Daicel Chemical Industries, Ltd., 2 mM aqueous copper sulfate solution:acetonitrile=6:4, 220 nm, 1.0 mL/min, rt). Ethyl acetate (400 mL) and activated carbon (500 mg) were added to the reaction mixture, and the mixture was adjusted to pH 1.1 with concentrated hydrochloric acid and filtered. The filtrate was partitioned to extract the title compound into the aqueous layer.

Example 12

Synthesis of L-2-t-butoxycarbonylamino-3,3-bis(4-fluorophenyl)propanoic acid An aqueous solution obtained in Example 11 of L-2-amino-3,3-bis(4-fluorophenyl)propanoic acid was adjusted to pH 8 with aqueous potassium hydrogencarbonate solution. Methanol (50 mL) and di-t-butyl dicarbonate (1.37 g, 6.3 mmol) were added, and the mixture was stirred at 37° C. for 3 hrs. The reaction mixture was adjusted to pH 1.1 with concentrated hydrochloric acid, and partitioned to extract the objective compound into the organic layer. The organic layer was concentrated and dried to give a solid (1.75 g). The solid was recrystallized to give the title compound (optical purity 99.3% ee, SUMICHIRAL OA-4100, hexane:methanol:2-propanol:trifluoroacetic acid=98:1:1:0.2, 210 nm, 1.0 mL/min, rt).

Example 13

Synthesis of D-2-amino-3,3-bis(4-fluorophenyl)propanoic acid

HPLC analysis of the organic layer separated in Example 11 revealed the presence of D-2-phenylacetylamino-3,3-bis(4-fluorophenyl)propanoic acid in a yield of 50% (78% ee, CHIRALPAK WH manufactured by Daicel Chemical Industries, Ltd., 2 mM aqueous copper sulfate solution:acetonitrile=6:4, 220 nm, 1.0 mL/min, rt). The organic layer was concentrated. Concentrated hydrochloric acid was added and the mixture was stirred at 100° C. for 16 hrs. The precipitated crystals were collected by filtration and dried to give the title compound (0.99 g, 78% ee, CHIRALPAK WH manufactured by Daicel Chemical Industries, Ltd., 2 mM aqueous copper sulfate solution:acetonitrile=6:4, 220 nm, 1.0 mL/min, rt).

Example 14

Synthesis of 2-acetylamino-3,3-bis(4-fluorophenyl)propanoic acid

To a solution of diethyl acetamidomalonate (1.09 g, 5 mmol) in N-methyl-2-pyrrolidone (4 mL) was added sodium hydride (219 mg, 5 mmol), and the mixture was stirred at room temperature for 1 hr. Bis(4-fluorophenyl)methylene bromide (990 mg, 4 mmol) was added, and the mixture was stirred at 50° C. for 4 hrs. After completion of the reaction, toluene (20 mL) and water (10 mL) were added to the reaction mixture and the mixture was partitioned. The obtained organic layer was washed twice with water (10 mL) and concentrated. Ethanol (4.5 mL) and 2M aqueous sodium hydroxide solution (5 mL) were added to the concentrated solution, and the mixture was stirred at 90° C. for 16 hrs. The reaction mixture was allowed to cool to 25° C., toluene (8 mL) and water (5 mL) were added, and the mixture was partitioned. The aqueous layer was concentrated to a half volume, and isopropyl acetate (8 mL) and water (10 mL) were added. The mixture was adjusted to pH 1.1 with concentrated hydrochloric acid and partitioned. The organic layer was washed with water (10 mL), concentrated and dried under vacuum to give the title compound (973 mg).

Example 15

Synthesis of diethyl(acetylamino)(bis(4-fluorophenyl)methyl)malonate

To a solution of diethyl acetamidomalonate (238 mg, 1.1 mmol) in N,N-dimethylformamide (1 mL) was added 55% sodium hydride (44 mg, 1.1 mmol), and the mixture was stirred at room temperature for 1 hr. Bis(4-fluorophenyl)methylene chloride (93 μL, 0.5 mmol) and tetra-n-butylammonium iodide (24 mg) were added, and the mixture was stirred at 50° C. for 16 hrs and then at 80° C. for 16 hrs. After completion of the reaction, HPLC quantitative analysis was performed to confirm 161 mg of the title compound (Inertsil ODS-2, 0.03 M phosphate buffer:acetonitrile=90:10-25:75 (20 min), 220 nm, 1.0 mL/min, rt).

Example 16

Synthesis of 2-acetylamino-3,3-bis(4-fluorophenyl)propanoic acid

Figure 2:
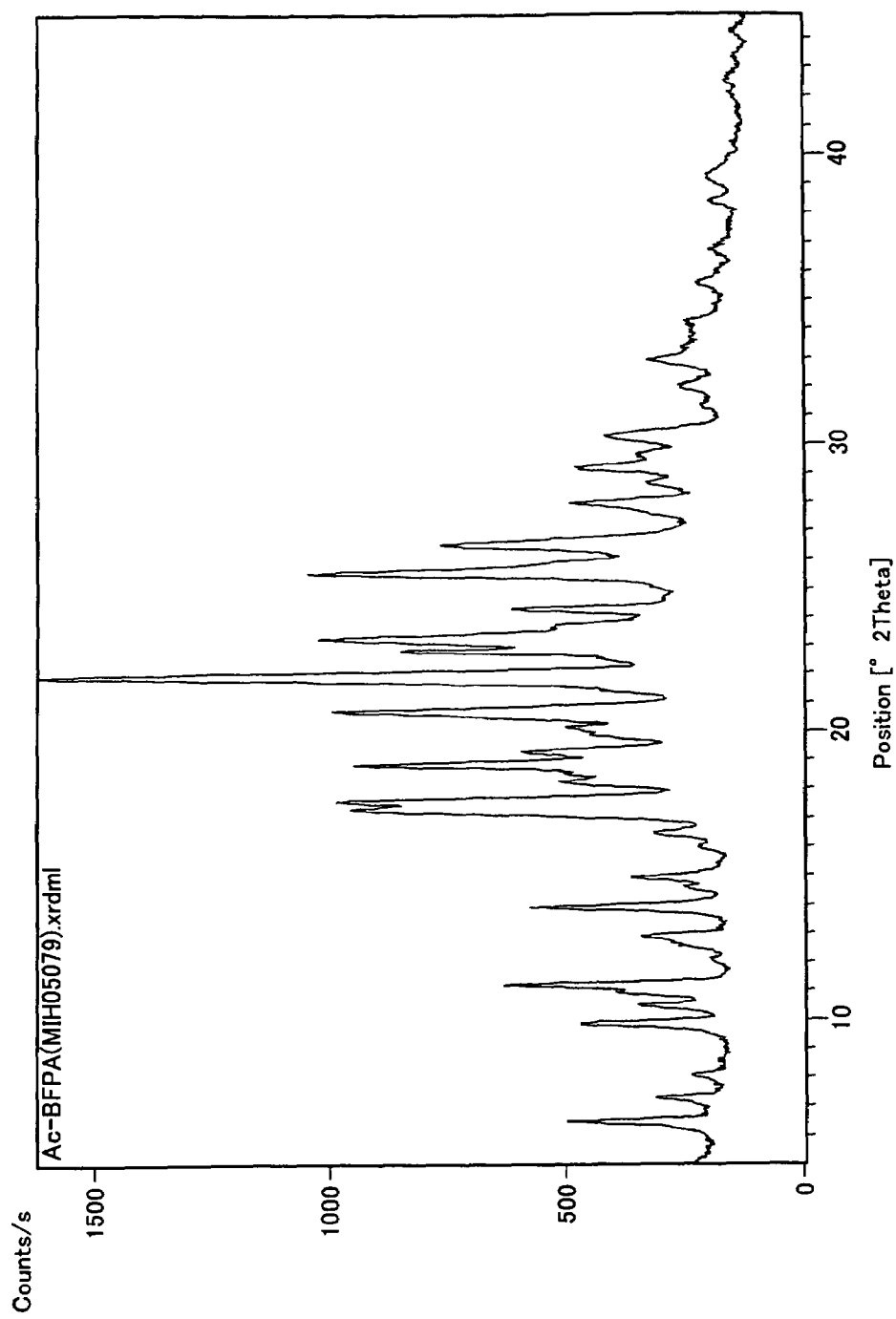
FIG. 2 is a powder X-ray diffraction chart of the wet crystal of racemic N-acetylbis(4-fluorophenyl)alanine in Example 16, wherein the vertical axis shows diffraction intensity and the axis of abscissas shows diffraction angles 2θ [deg].
Figure 3:
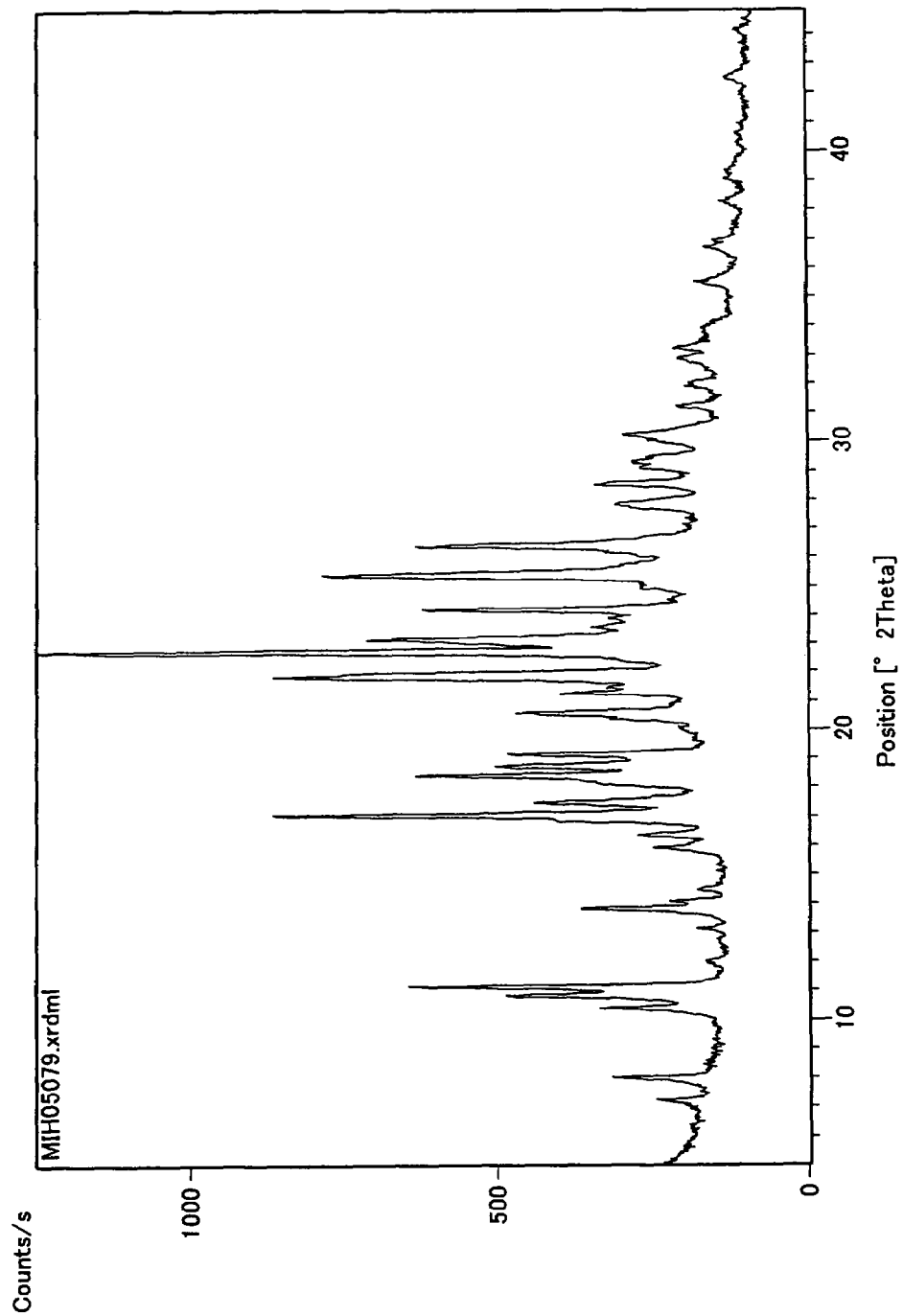
FIG. 3 is a powder X-ray diffraction chart of the crystal of racemic N-acetylbis(4-fluorophenyl)alanine after drying in Example 16, wherein the vertical axis shows diffraction intensity and the axis of abscissas shows diffraction angles 2θ [deg].

To a solution (1.25 M) of diethyl acetamidomalonate (5.17 g, 23.80 mmol) in N-methyl-2-pyrrolidone (18.2 mL) was added potassium t-butoxide (2.77 g, 24.69 mmol), and the mixture was stirred at room temperature for 1 hr. A toluene solution (21.79 g) of bis(4-fluorophenyl)methylene chloride (4.54 g, 19.02 mmol) and potassium iodide (3.19 g, 19.10 mol) were added, and the mixture was stirred at 70° C. for 6 hrs. After completion of the reaction, 2M aqueous sodium hydroxide solution (45 mL) was added to the reaction mixture, and the mixture was stirred at 60° C. for 5 hrs. The reaction mixture was allowed to cool to room temperature and partitioned. The aqueous layer was adjusted to pH 7.0 with concentrated hydrochloric acid (4.4 mL). Ethyl acetate (30 mL) was added, and then concentrated hydrochloric acid (6.9 mL) was added. The mixture was partitioned and the aqueous layer was extracted with ethyl acetate (6 mL). The organic layers were combined, and the content of the title compound was examined by HPLC to find 5.678 g thereof contained in the organic layer. The organic layer was successively washed with 2M hydrochloric acid (9 mL, three times) and saturated brine (4.5 mL), and concentrated. Toluene (13.5 mL) was added to the concentrated solution, and the mixture was concentrated at 50° C. Toluene (13.5 mL) was added again, and the mixture was stirred for 30 min and cooled to 0° C. over 5 hrs, which resulted in the precipitation of white crystals. The crystals were collected by filtration to give wet crystals. The powder X-ray (Cu—Kα ray) of the wet crystals showed characteristic peaks at 17.1°, 17.6°, 18.8°, 20.7°, 21.8°, 22.0°, 22.7°, 23.1° and 25.4°, as shown in FIG. 2. The wet crystals were dried under reduced pressure to give the title compound (5.39 g) as dry crystals. The powder X-ray (Cu—Kα ray) of the dry crystals showed characteristic peaks at 17.1°, 21.8°, 22.0°, 22.7°, 23.1° and 25.4°, as shown in FIG. 3.

Example 17

Synthesis of 2-acetylamino-3,3-bis(4-fluorophenyl)propanoic acid

Figure 4:
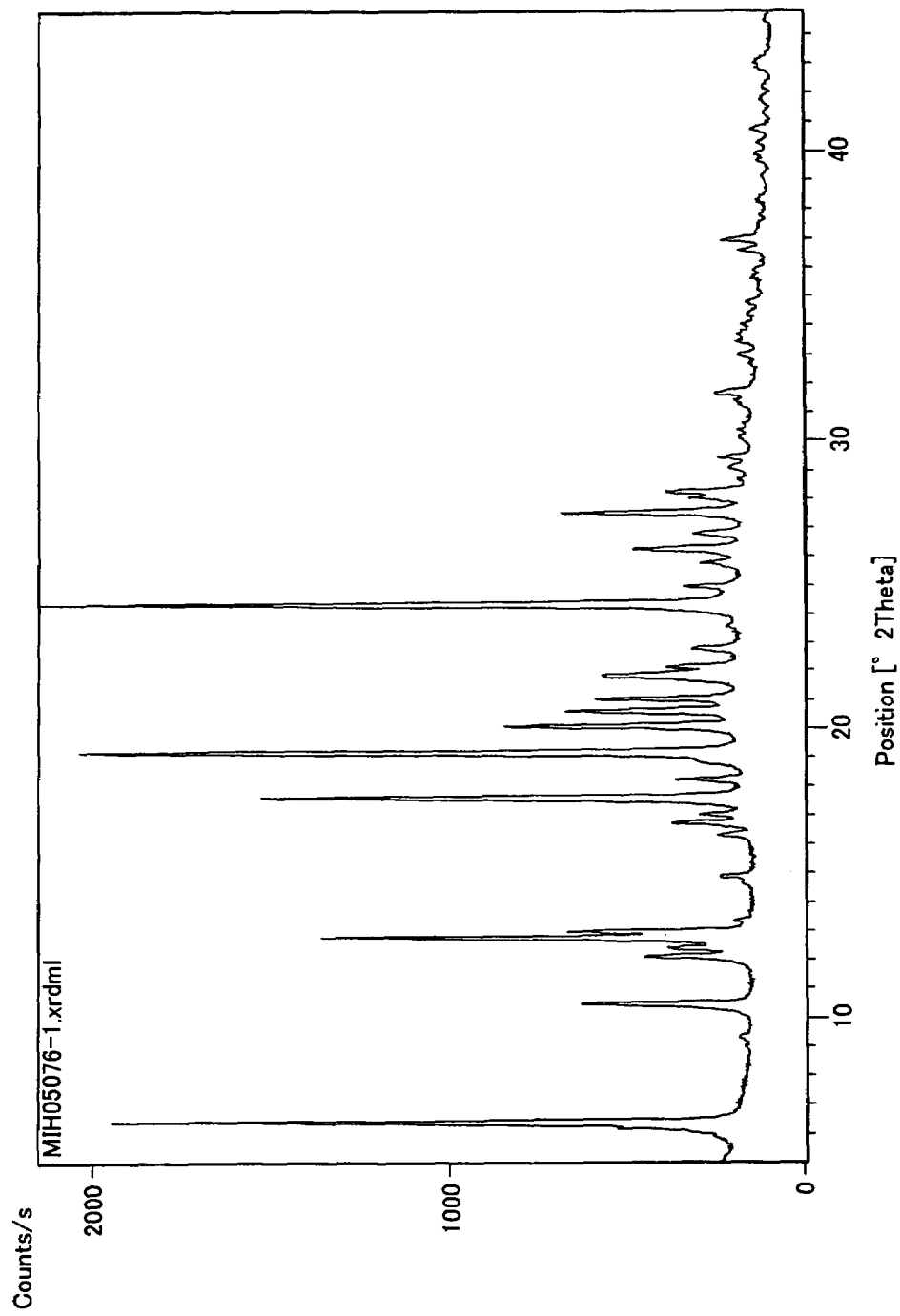
FIG. 4 is a powder X-ray diffraction chart of the wet crystal of racemic N-acetylbis(4-fluorophenyl)alanine in Example 17, wherein the vertical axis shows diffraction intensity and the axis of abscissas shows diffraction angles 2θ [deg].

To a solution (1.25 M) of diethyl acetamidomalonate (5.14 g, 23.66 mmol) in N-methyl-2-pyrrolidone (19.0 mL) was added sodium t-butoxide (2.38 g, 24.76 mmol), and the mixture was stirred at room temperature for 1 hr. A toluene solution (22.07 g) of bis(4-fluorophenyl)methylene chloride (4.54 g, 19.02 mmol) and potassium iodide (3.17 g, 19.10 mol) were added, and the mixture was stirred at 60° C. for 6 hrs. After completion of the reaction, 2M aqueous sodium hydroxide solution (45 mL) was added to the reaction mixture, and the mixture was stirred at 60° C. for 4 hrs. The reaction mixture was allowed to cool to room temperature and partitioned. The aqueous layer was adjusted to pH 7.0 with concentrated hydrochloric acid (4.4 mL). Ethyl acetate (30 mL) was added, and then concentrated hydrochloric acid (6.9 mL) was added. The mixture was partitioned and the aqueous layer was extracted with, ethyl acetate (6 mL). The organic layers were combined, and the content of the title compound was examined by HPLC to find 5.914 g thereof contained in the organic layer. The organic layer was successively washed with 2M hydrochloric acid (9 mL, three times) and saturated brine (4.5 mL), and concentrated at 40° C. to about ¼ in volume. The organic layer was cooled to allow crystal precipitation. After cooling to 0° C., the crystals were collected by filtration to give wet crystals. The powder X-ray (Cu—Kα ray) of the wet crystals showed characteristic peaks at 12.8°, 17.6°, 19.2° and 24.3°, as shown in FIG. 4.

Example 18

Synthesis of 2-acetylamino-3,3-bis(4-fluorophenyl)propanoic acid

To a solution (1.1 M) of diethyl acetamidomalonate (1.15 g, 5.29 mmol) in N-ethyl-2-pyrrolidone (4.0 mL) was added potassium t-butoxide (0.58 g, 5.41 mmol), and the mixture was stirred at room temperature for 1 hr. Bis(4-fluorophenyl)methylene chloride (1.0 g, 4.21 mmol) and potassium iodide (0.70 g, 4.21 mol) were added, and the mixture was stirred at 60° C. for 6 hrs. After completion of the reaction, toluene (5 mL) and 2M aqueous sodium hydroxide solution (5 mL) were added to the reaction mixture, and the mixture was stirred at 60° C. for 5 hrs. The reaction mixture was allowed to cool to room temperature and partitioned. The aqueous layer was adjusted to 7.0 with concentrated hydrochloric acid. Ethyl acetate (8 mL) was added, and then concentrated hydrochloric acid was added. The mixture was partitioned and the aqueous layer was extracted with ethyl acetate (2 mL). The organic layers were combined, and the content of the title compound was examined by HPLC to find 1.10 g thereof contained in the organic layer (Inertsil ODS-2, 0.03 M phosphate buffer:acetonitrile=90:10-25:75 (20 min), 220 nm, 1.0 mL/min, rt).

INDUSTRIAL APPLICABILITY

According to the present invention, an optically active diphenylalanine compound, which is useful as an intermediate for anti-HIV drugs, dipeptidyl peptidase inhibitors and the like, can be produced conveniently in a high yield by substrate-specifically reacting a novel diphenylalanine compound or a salt thereof with a penicillin amidase. Furthermore, racemic N-acetyldiphenylalanine and racemic N-acetylbis(4-fluorophenyl)alanine can be obtained at a high purity in the form of crystals convenient for preservation and transportation.

This application is based on patent application Nos. 2005-137637 and 2005-209795 filed in Japan, the contents of which are hereby incorporated by reference.

The invention claimed is:

1. A method of producing a diphenylalanine compound represented by formula (4) or a salt thereof, which comprises:
   (a): reacting a diphenylmethylene halide compound represented by formula (1):

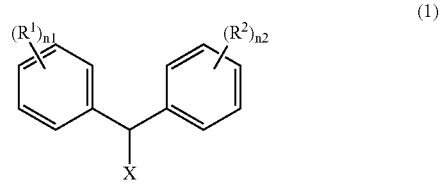

wherein
$R^1$ and $R^2$ are each independently a halogen atom, an alkyl group, an alkoxy group, an amino group, a nitro group or a hydroxyl group,
$n^1$ and $n^2$ are each independently an integer of 0-5, and
X is a chlorine atom, a bromine atom or an iodine atom,
with a malonic acid diester compound represented by formula (2):

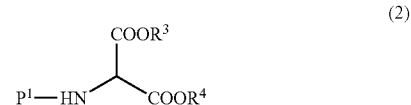

wherein
$R^3$ and $R^4$ are each independently an alkyl group or an aralkyl group, or $R^3$ and $R^4$ in combination form an alkylene group, and
$P^1$ is an amino-protecting group,
in at least one organic solvent selected from the group consisting of N-methyl-2-pyrrolidone, N-ethyl-2-pyrrolidone, N,N-dimethylformamide, and mixtures thereof, in the presence of at least one base selected from the group consisting of an alkali metal hydride, an alkali metal t-butoxide, and mixtures thereof, to give a diester compound represented by formula (3):

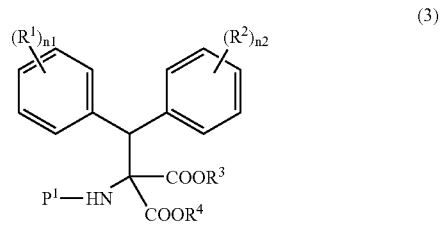

wherein each symbol is as defined above; and (b): subjecting said diester compound to hydrolysis and decarboxylation, to give said diphenylalanine compound represented by formula (4):

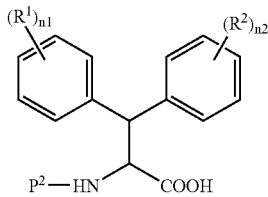

(4)

wherein $R^1$, $R^2$, $n^1$ and $n^2$ are as defined above, and $P^2$ is a hydrogen atom or an amino-protecting group, or a salt thereof.

2. The method of claim 1, wherein $P^2$ is a hydrogen atom, an acetyl group or a phenylacetyl group.

3. The method of claim 1, wherein said reacting of said diphenylmethylene halide compound represented by formula (1) with said malonic acid diester compound represented by formula (2) is carried out in the presence of at least one base which is selected from the group consisting of sodium hydride, sodium t-butoxide, potassium t-butoxide, and mixtures thereof.

4. The method of claim 1, wherein said reacting of said diphenylmethylene halide compound represented by formula (1) with said malonic acid diester compound represented by formula (2) is carried out in at least one organic solvent which is selected from the group consisting of N-methyl-2-pyrrolidone, N-ethyl-2-pyrrolidone, and mixtures thereof.

5. The method of claim 1, wherein $R^1$ and $P^2$ are each a fluorine atom.

6. The method of claim 1, wherein $P^3$ and $R^4$ are each an ethyl group.

7. The method of claim 1, wherein $P^1$ is an acetyl group or a phenylacetyl group.

8. The method of claim 1, wherein X is a chlorine atom or a bromine atom.

9. The method of claim 1, wherein said reacting of said diphenylmethylene halide compound represented by formula (1) with said malonic acid diester compound represented by formula (2) is carried out in the presence of an iodine compound or a bromine compound.

10. The method of claim 1, wherein said reacting of said diphenylmethylene halide compound represented by formula (1) with said malonic acid diester compound represented by formula (2) is carried out in the presence of a metal iodide or a quaternary ammonium iodide.

* * * * *